United States Patent [19]

Southgate

[11] 4,292,672

[45] Sep. 29, 1981

[54] INSPECTION SYSTEM FOR DETECTING DEFECTS IN REGULAR PATTERNS

[75] Inventor: Peter D. Southgate, Princeton, N.J.

[73] Assignee: RCA Corporation, New York, N.Y.

[21] Appl. No.: 21,822

[22] Filed: Mar. 19, 1979

[51] Int. Cl.³ .................... G01N 33/34; G01N 33/36
[52] U.S. Cl. ................................. 364/507; 356/239;
358/106; 364/573; 364/728
[58] Field of Search ............... 356/237, 239; 250/562,
250/563, 571, 572; 358/101, 106; 364/507, 515,
573, 819, 728; 340/146.3

[56] References Cited

U.S. PATENT DOCUMENTS

| | | | |
|---|---|---|---|
| 3,614,232 | 10/1971 | Mathisen | 356/239 |
| 3,658,420 | 4/1972 | Axelrod | 356/152 |
| 3,738,752 | 6/1973 | Heinz et al. | 356/239 |
| 3,882,461 | 5/1975 | Vinnemann et al. | 340/146.3 ED |
| 3,887,762 | 6/1975 | Uno et al. | 358/106 |
| 3,958,127 | 5/1976 | Faulhaber et al. | 356/239 |
| 3,963,354 | 6/1976 | Feldman et al. | 356/239 |
| 3,972,616 | 8/1976 | Minami et al. | 356/239 |
| 3,982,426 | 9/1976 | Newhouse et al. | 369/507 |
| 4,005,281 | 1/1977 | Faulhaber et al. | 364/507 |
| 4,149,120 | 4/1979 | Richter | 364/573 |

Primary Examiner—Felix D. Gruber
Attorney, Agent, or Firm—Eugene M. Whitacre; Glenn H. Bruestie; Dennis H. Irlbeck

[57] ABSTRACT

The inspection system detects defects in regular patterns wherein the elements of the patterns may have variations in period. The system includes means for scanning and detecting the elements of a pattern to produce an original output signal indicative of the pattern. Means then delay the output signal from the scanning and detecting means to produce a delayed output signal. Next, any deviation in period between the original output signal and the delayed output signal is detected by suitable means. Means now match the periods of the original and delayed output signals, and other means correlate the matched original and delayed output signals.

8 Claims, 14 Drawing Figures

DEVICES:
A BUFFER AMPLIFIERS
B D-TYPE FLIP-FLOP
C AND GATE
D ANALOG GATE
E DIFFERENTIAL AMPLIFIER

| OPAQUE / CLEAR | 1/2 2/4 | 1/2 3/5 | 1 2/4 | 1 3/5 |
|---|---|---|---|---|
| 1/2 2/4 | 0 | 2 | 8 | A |
| 1/2 3/4 | 1 | 3 | 9 | B |
| 1 2/4 | 4 | 6 | C | E |
| 1 3/4 | 5 | 7 | D | F |

INSPECTION SYSTEM FOR DETECTING DEFECTS IN REGULAR PATTERNS

BACKGROUND OF THE INVENTION

This invention relates to the detection of defects in regular periodic patterns and particularly to an inspection system for detecting defects in such patterns wherein the elements of the patterns have variable periodicity. Although the present invention may be utilized to detect defects in many different types of regular periodic patterns, it hereinafter will be described with respect to the detection of defects in photographic master plates used in forming shadow masks of color television picture tubes.

Shadow masks used in color picture tubes are manufactured by a photolithography method in which a glass working plate with a suitable pattern on it is pressed against a photoresist coated steel sheet while the photoresist material is exposed by a suitable light source. During the many repetitions of this procedure, the pattern on the glass plate can become damaged. Either small portions of the black dots or bars which form the pattern can become torn off, or dirt particles can become pressed into the pattern. Masks made from defective plates will be faulty and must be discarded. Therefore, there is a need to periodically inspect the glass working plates.

Small defects of the dark dots or bars superimposed on a light background are very difficult to see when the pattern is viewed without magnification. This is in marked contrast to the negative pattern, such as is formed by the finished shadow mask, where enlarged or extra holes are quite visible, particularly to a trained observer. One way of enhancing visibility of some defects in a working plate is to superimpose a closely matched negative plate. Missing parts of the pattern will then show up as bright transmission spots. If the negative is shifted, extra dark spots can be given an enhanced visibility. However, this technique has a limited usefulness. For a satisfactory complete inspection, up to now it has been necessary to visually scan the plate under magnification, a process taking about 2 hours per plate.

A problem involved in automating the inspection of regular periodic patterns occurs when the pattern periodicity that is the element-to-element spacing of the pattern, varies over the pattern. The present invention solves this problem while providing an essentially automatic inspection system.

SUMMARY OF THE INVENTION

An inspection system is provided which detects defects in regular patterns wherein the elements of the patterns have variations in period. The system includes means for scanning and detecting the elements of a pattern to produce an original output signal indicative of the pattern. Means then delay the output signal from the scanning and detecting means to produce a delayed output signal. Next, any deviation in period between the original output signal and the delayed output signal is detected by suitable means. Means now match the periods of the original and delayed output signals, and other means correlate the matched original and delayed output signals.

DETAILED DESCRIPTION

Figure 4:
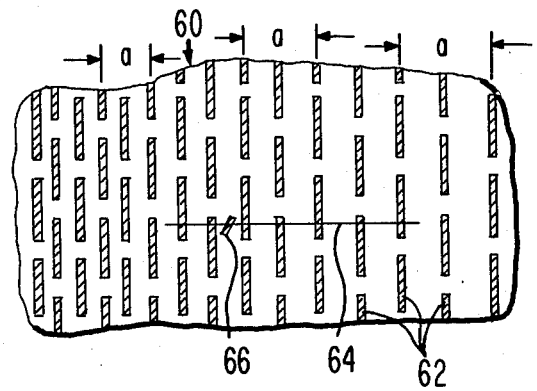
FIG. 4 is a partial view of a pattern on a working plate.

The present inspection system is used for scanning a regular periodic pattern, such as a negative aperture pattern on a glass working plate used for exposing photoresist material on a metal sheet in the construction of shadow masks for color television picture tubes. One such aperture pattern is shown in FIG. 4 wherein the period is the horizontal element-to-element spacing. Scanning of a pattern takes two forms. The first is the gross mechanical scanning of a video sensor in a specific manner over the pattern while the second is the electrical scanning of a line array target within the video sensor. The purpose of scanning patterns is to determine and locate defects in the patterns. The defects are discovered by a portion of the inspection system which autocorrelates the sensor output, also called the video signal, with itself. Autocorrelation in one form of the invention is accomplished by providing a delay in the video signal and then comparing the signals by a method such as subtraction of the delayed video signal from the original video signal. Any signal remaining after this procedure is an error signal indicating the presence of a defect. This autocorrelating technique will provide a meaningful result when the periodicity of the pattern is uniform. However, when the pattern periodicity is nonuniform, such as in the pattern of FIG. 4, the present invention provides means for compensating for the nonuniformity so that autocorrelation may be performed.

The present inspection system, which may be implemented in either an analog form or in a digital form, handles the problem of autocorrelating a video signal when the periodicity in elements of a pattern is nonuniform. In the analog system, the video signal is delayed a set time which is related to the anticipated pattern period and a difference signal is obtained by comparing the original video signal with the delayed video signal. The difference signal is then used to control video sensor scan rate so that the period of the video signal output from the video sensor matches the period of the delayed video signal. In the digital system, scan rate is held constant and the time of computer storage of the delayed video signal is varied in order to match periodicity of the original and delayed signals.

Figure 1:
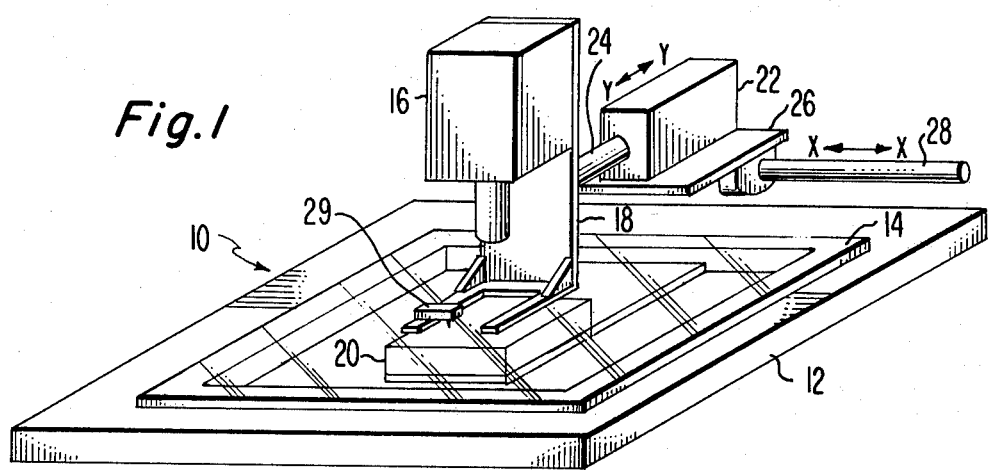
FIG. 1 is a perspective view of a video sensor scan apparatus including a glass working plate on a base.

The components and functions of each type of inspection system will now be discussed in greater detail. First, the analog system is presented and then the digital system. One embodiment of a mechanical scanning apparatus 10 of the present inspection system is shown in FIG. 1. The apparatus 10 includes a base 12 on which a glass working plate 14, having a regular pattern thereon, is mounted. The base 12 supports the edges of the plate 14 and is open in the center so as not to obstruct the photographic pattern on the plate 14. A video sensor 16, such as a solid state photodiode array, is mounted on a platform 18 directly above the working plate 14. A light box 20 is located underneath the plate 14 directly below the video sensor 16. The platform 18 is moveable in two directions, X-X and Y-Y. Movement of the sensor 16 in the Y-Y direction is by actuation of a suitable unit 22 such as a pneumatic cylinder or electrical selenoid, attached to the platform 18 by a shaft 24. The unit 22 sits on a second platform 26 which is moveable along a shaft 28 by another unit, not shown. A marking unit 29 also is shown attached to a portion of the platform 18 for indicating areas of defects on the working plate.

The video sensor 16 in the system may be a camera having a lens for collecting light passing through a pattern and for imaging the pattern onto a photoelectric sensor within the camera. The light is diffused to provide a wide range of incident light angles to reduce sensitivity to scratches. The sensor reads light transmitted through a glass plate on which an emulsion pattern is located. The image lens, such as a Vivitar 55 mm 2.8 Automacro lens, is housed in a light tight enclosure with a solid state line scanner such as a 1728 element photodiode array, commercially available from the Reticon Corporation. The magnification of the lens is 1.5. Each scanner element is 15 $\mu$m wide which corresponds to 0.4 mils on the working plate pattern. The scanner elements integrate collected light, and when addressed, discharge the integrated signal. Each scanner element acts independently, so that output signal is a series of charge pulses. These pulses are processed in a sample and hold amplifier, and the resultant output of the camera is a boxcar video signal in which each level is representative of the amount of light collected by that element during one scan period.

Figure 2:
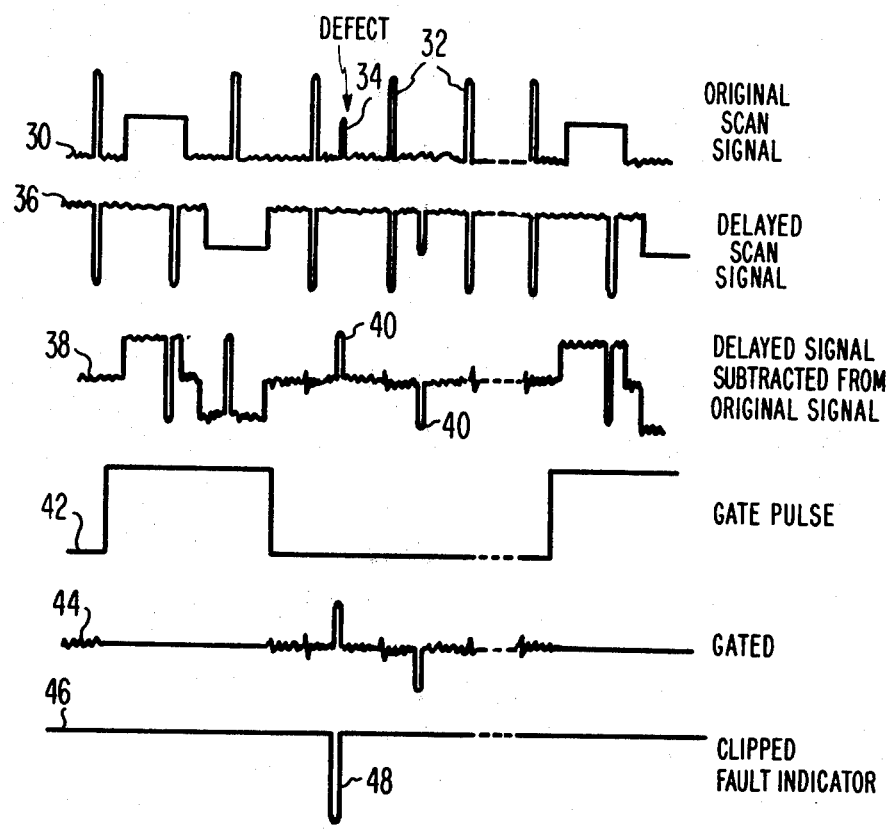
FIG. 2 is a schematic diagram showing a series of analog waveforms illustrating correlation of a video signal with itself.

The principle of autocorrelating the output signal from the video sensor 16 in an analog system is illustrated in the waveforms shown in FIG. 2. The upper waveform 30 is the video sensor output signal which consists of a series of parallel narrow bright bars 32 indicating elements of the pattern being scanned by the video sensor. An extra pulse 34 is present because of a defect in the pattern. The second waveform 36 shows the original waveform 30 inverted and delayed one period. The second waveform 36 is next subtracted from the first waveform 30 to obtain a third waveform 38. The defect signal 40 appears prominently in both polarities in the third waveform 38. Also shown in the third waveform 38 is some noise and extra small spikes which can appear if the delay time varies slightly from one exact period. The fourth waveform 42 is a gating waveform for selecting those portions of the third subtracted waveform 38 during which a pertinent portion of the video signal occurs in both the original and delayed waveforms, 30 and 36, respectively. The fifth waveform 44 shows a portion of the third subtracted waveform 38 passed by the fourth gating waveform 42. Finally, the sixth waveform 46 shows the gated signal clipped at a suitable threshold level thereby giving an unambiguous indication of defects of greater than a certain size, such as the spike 48.

Figure 3:
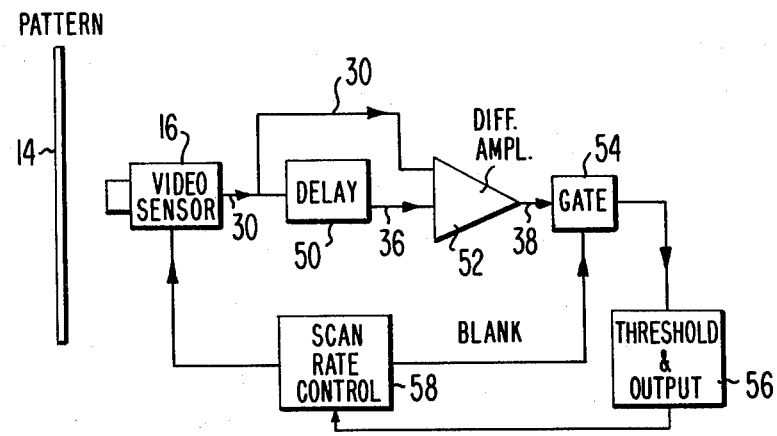
FIG. 3 is a block diagram of autocorrelation components in one embodiment of the present inspection system.

Analog circuits to achieve each of the foregoing functions are well known in the art. A block diagram of the interconnection of these circuits is shown in FIG. 3. The output 30 of the video sensor 16 is fed both to a suitable delay line 50 such as an acoustic glass line or a solid state CCD device and to a differential amplifier 52. The output 36 of the delay line 50 is also fed into the differential amplifier 52. The output of the differential amplifier 52 is the subtracted waveform 38. This output 38 is fed into a gating circuit 54 which gates the subtracted waveform 38 to obtain the gated waveform 44. The gated waveform 44 is fed to the threshold and output circuit 56 where it is clipped and any defects remaining are indicated. The block diagram also includes a scan rate control unit 58 with inputs to both the camera 16 and gate circuit 54.

Although the foregoing autocorrelation example has been described with respect to a pattern of uniform periodicity, the periodicity of the pattern may vary across the scan distance. In such case, the video signal must be linearized before the correlation processing can be performed. The periodicity of the video signal may vary in a linear fashion requiring two variables to specify its form, or the periodicity may vary in a quadratic or higher order fashion requiring three or more variables. For each variable, an error signal is required, and for each error signal, the video signal must be sampled at an appropriate point along the scan.

Figure 5:
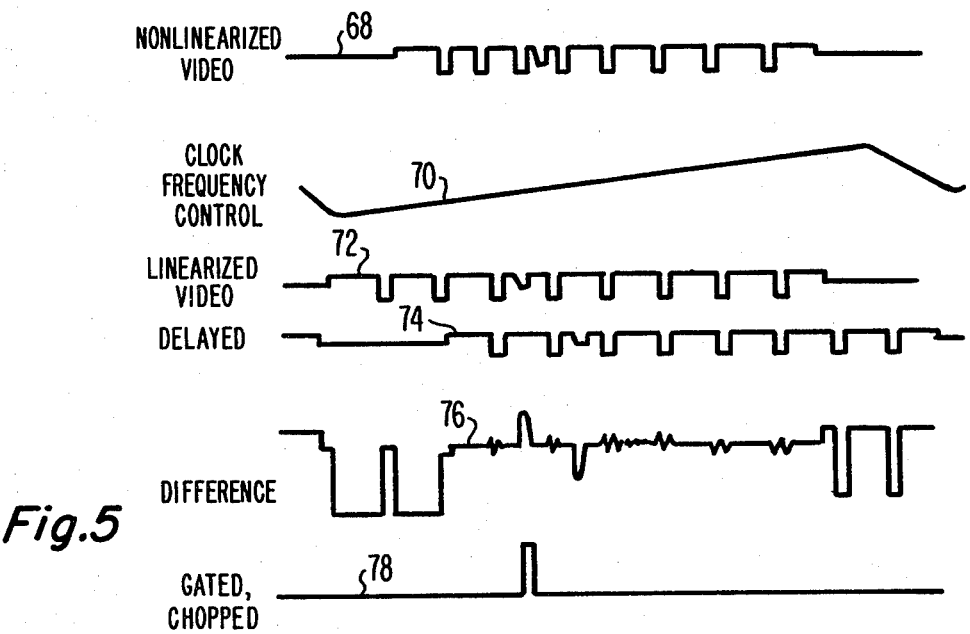
FIG. 5 is a schematic diagram showing a series of analog waveforms illustrating linearization of a linearly varying video signal.

FIG. 4 shows a portion of a pattern 60 having a linear variation in periodicity of elements 62 of the pattern. The period in the pattern 60 is labelled "a" and, as can be seen, varies horizontally across the pattern. The solid horizontal line 64 on the pattern 60 is the image formed on a solid state photodiode linear array which is read out by a clock of variable frequency. The small mark 66 on the pattern represents a defect. If the output rate of the photodiode linear array were not linearized, it would appear as the first waveform 68 in FIG. 5. However, the video sensor output can be linearized by appropriately changing the scan rate. The second waveform 70 of FIG. 5 shows a saw-tooth variation in clock frequency that is necessary to change the scan rate to obtain the linearized video signal 72 shown as the third waveform of FIG. 5. When this change in frequency is arranged to be proportionally higher as the wide-spaced pattern elements are read out, the video pattern period will remain substantially constant. Subsequent waveforms of FIG. 5 show the delayed video signal 74, the difference signal 76 and the gated chopped signal 78.

Figure 6:
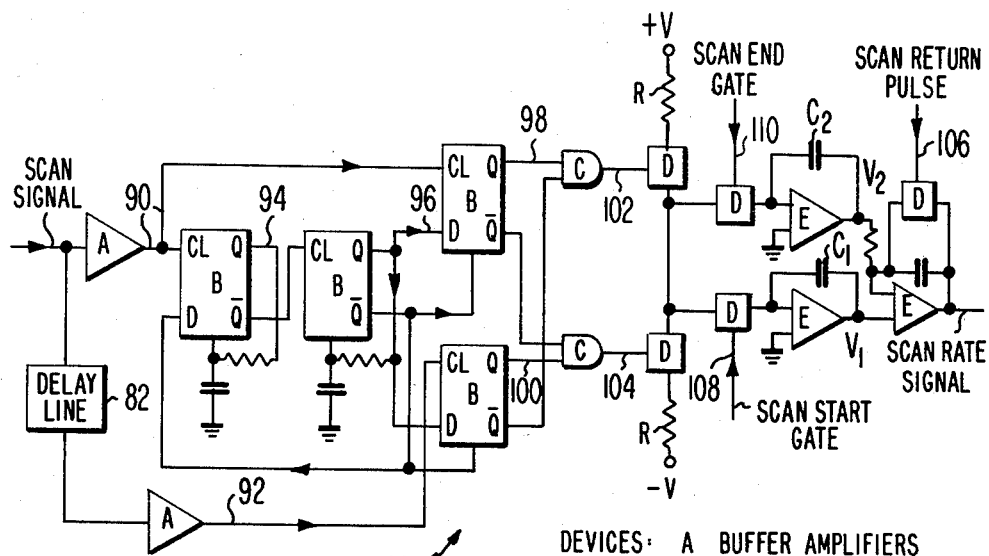
FIG. 6 is a circuit diagram of an analog linearization circuit.
Figure 7:
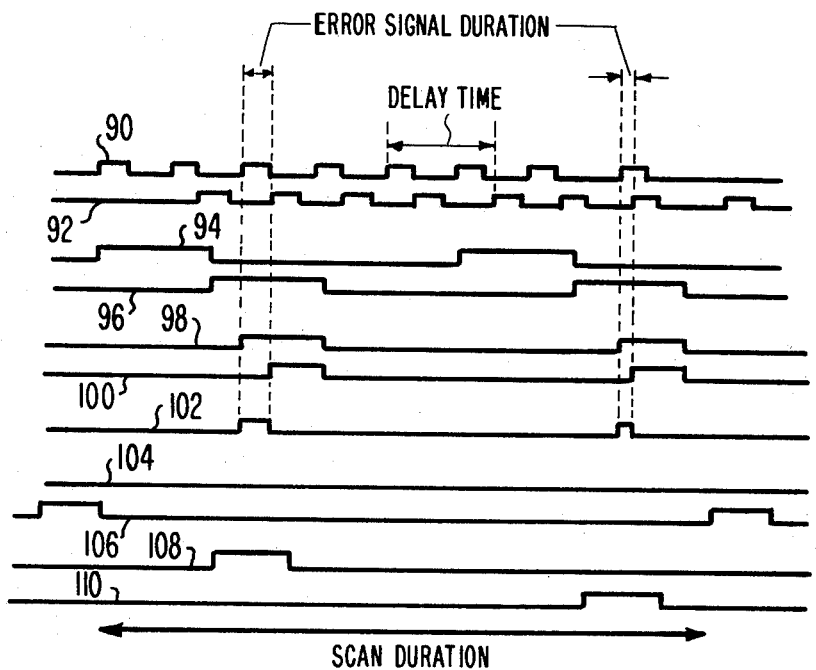
FIG. 7 is a schematic diagram showing a series of waveforms for obtaining a linearizing signal.

The appropriate saw-tooth waveform 70 of FIG. 5 can be generated by an analog circuit 80 shown in FIG. 6. This circuit 80 is an integrating circuit wherein the initial value and rate of rise of the output signal are determined by the voltages on the two capacitances $C_1$ and $C_2$. If the originally generated waveform does not give accurate linearization, the capacitor voltages are incremented by an error signal which drops to zero only when linearization has been achieved. The portion of the circuit 80 preceding the capacitors $C_1$ and $C_2$ has the function of generating these incrementing voltages. The functioning of the circuit 80 can be seen from the waveforms of FIG. 7. Essential to the operation of the circuit 80 is a delay line 82 which delays the video signal by a time equal to a desired period or a multiple thereof. The first waveform 90 in FIG. 7 shows the video signal as it comes from the scanning sensor. The second waveform 92 shows the video signal after it has been delayed a period greater than the desired period but less than twice the desired period. The video signal triggers a pulse generator having an output waveform 94 which in turn triggers a second pulse generator having an output waveform 96. The waveform 96 from the second pulse generator gives windows for selecting video pulses near the beginning and end of the scan. Waveforms 98 and 100 are then generated by the leading edges of the initial video and delayed video pulses which fall within the windows of the waveform 96. If the initial video leads the delayed video, the difference pulse is applied to a switch which charges the capacitor positive during the pulse period, while if the delayed video leads, the capacitor is charged negative. This difference pulse, appropriately signed, is the error signal 102 or 104 which corrects the clock frequency control. A further pair of switches are arranged to divert the error signal to $C_1$ or $C_2$ depending on whether the window is located at the start or finish of the scan. The remaining three waveforms in FIG. 7 are the scan return pulse 106, the scan start gate signal 108 and the scan end gate signal 110.

Figure 8:
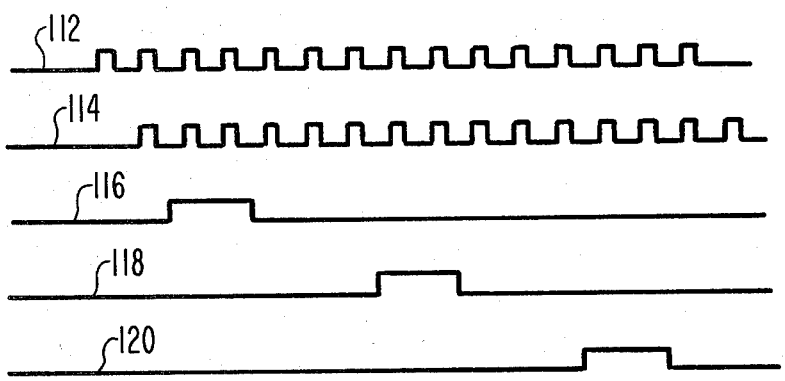
FIG. 8 is a schematic diagram showing a series of waveforms for linearizing a video signal varying in a quadradic manner.

The foregoing described linearization circuit 80 will provide an appropriate correction for a linear variation in the spatial pattern periodicity. However, if the pattern variation has quadratic or higher components, more than two capacitors and voltages will be required to correct for the variation. These voltages will correspond to error signals taken at various points along the scan and are fed into a control waveform generating circuit containing several stages of integration. The error signals between a video signal 112 and a delayed video signal 114 from the start, middle and end of a scan are sampled by the windows in gating waveforms 116, 118 and 120 as shown in FIG. 8. These error signals are used to increment the control voltages $V_1$, $V_2$ and $V_3$. However, first these three voltages are converted into another set of three voltages, as follows, using amplifier-resistor networks well known in the art.

$V_a = 2V_1 = 4V_2 + 3V_3$ $V_b = -2V_1 + 4V_2 - V_3$ $V_c = V_1$

Figure 9:
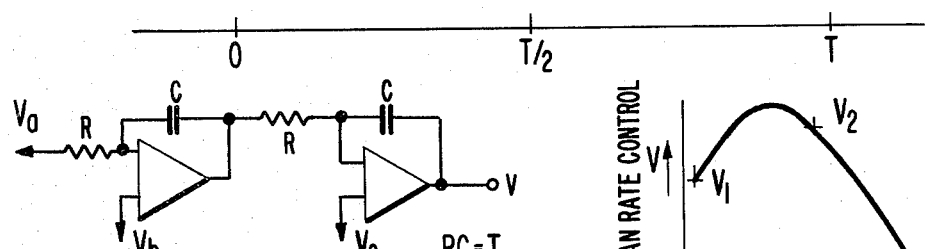
FIG. 9 is a circuit diagram for producing a quadradic output.

These voltages are then fed into the circuit of FIG. 9 which will give a quadratic output of the form, $$V = 2(V_1 - 2V + V_3)\left(\frac{t}{T}\right)^2 +$$

Figure 10:
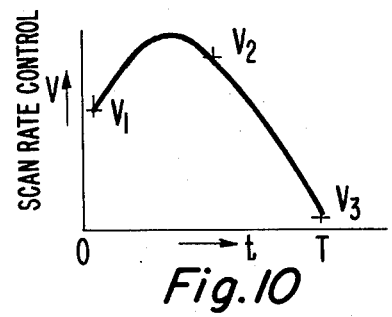
FIG. 10 is a graph showing the scan rate control signal for providing quadradic correction.

-continued $$(-3V_1 + 4V_2 - V_3)\left(\frac{t}{T}\right) + V_1$$

where T is the scan time. This waveform has the property of passing through voltages $V_1$, $V_2$ and $V_3$ when $t/T=0$, $\frac{1}{2}$ and 1 respectively, as shown in FIG. 10.

The embodiment described above shows only one way in which the present invention can be applied. In general, the video sensor which converts the pattern into a signal could be any of a variety of optical, electrical, mechanical or other detectors, scanned in any way which is controlled by a waveform determined by the stored control voltages. Similarly, the signal delay line may be made in a number of well established ways.

Figures 11, 14:
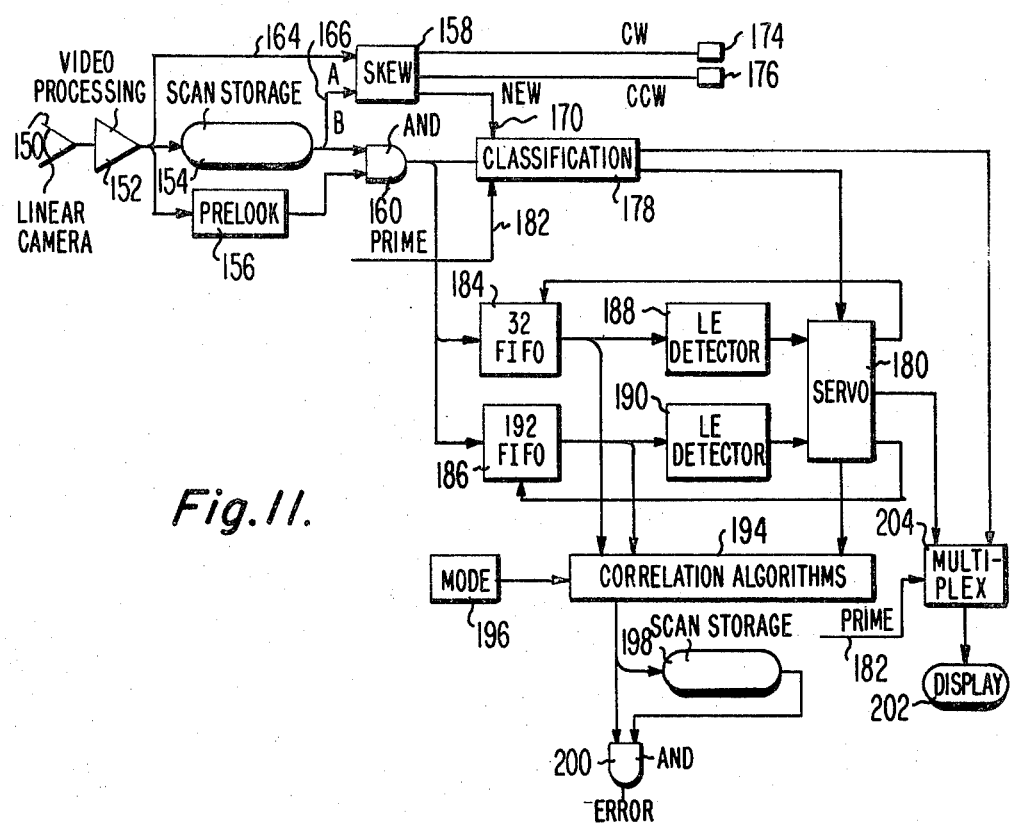
FIG. 11 is a circuit diagram of a digital inspection system.
FIG. 14 is a table showing the various optional settings for the mode unit of the circuit of FIG. 11.

A circuit incorporating a digital embodiment is shown in the block diagram of FIG. 11. In this embodiment, digital techniques are used exclusively after the video signal has been quantized, with the various logic modules locked into a crystal controlled clock. The digital system is fully adaptive to a wide range of patterns, with the only operator adjustment necessary being alignment of the photographic plate to a video sensor, such as a camera, utilizing controlled indicators.

In the digital system, the video sensor scan rate is not linearized as in the analog system. Instead, the equivalent result is achieved by controlling the time of storage of the video signal so that the original and delayed video signals are in phase when fed into the correlation unit.

The output signal from a camera 150 is fed into video processing circuits 152. Three functions are performed in the video processing circuit 152. The first function is automatic gain control for maintaining a peak to peak video signal (e.g. 5 volts) over a range of inputs (e.g. from $\frac{1}{2}$ volt to 2 volts). Automatic gain control action compensates for aging of the lamp used to illuminate the pattern, component tolerances, dust in the optics, and any other effects that would change video amplitude over a long term. The second function of the video processing circuits is to minimize shading, the result of a non-flat illumination field creating a bowed video baseline. Finally, after automatic gain control and shading elmination, the video signal is quantized into a binary digital signal. Nominally, the quantizing level is set to 50%.

The output of the video processing circuits 152 is fed to a scan storage unit 154, a prelock unit 156 and a skew unit 158. The scan storage unit 154 consists of a 2048 stage shift register. Data is entered in the shift register during one scan, and appears on the output exactly one scan later. Timing and control is designed to recycle every 2049 bits with a 1 bit dead time. There are 1728 elements active on the signal from the camera and 321 bits of blanking are used for data processing later in the block diagram.

The purpose of the prelook unit 156 is to gate out of the camera video signal incomplete patterns prior to comparative analysis. These incomplete patterns may be either in the beginning or end of a scan and are due to a number of causes. For example, the camera may be aligned in such a manner that the first pattern elements fall in the middle of an opaque slit. Also, some patterns may actually have incomplete slits around the edges. Or finally, a compare error may be generated on the pattern trailing edge, due to absence of a neighbor pattern for comparison. With the prelook circuit, the video from video processing circuits 152 are analyzed, starting and ending locations are stored, and then when video emerges from the scan storage during the next scan, the unwanted video is removed via an "And" gate 160.

Figure 12:
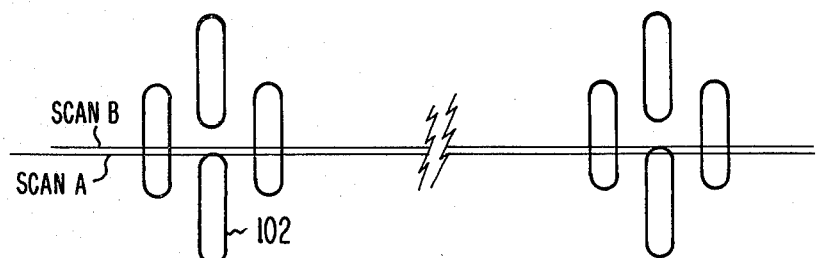
FIG. 12 is a schematic diagram showing scan lines on portions of a pattern.
Figure 13:
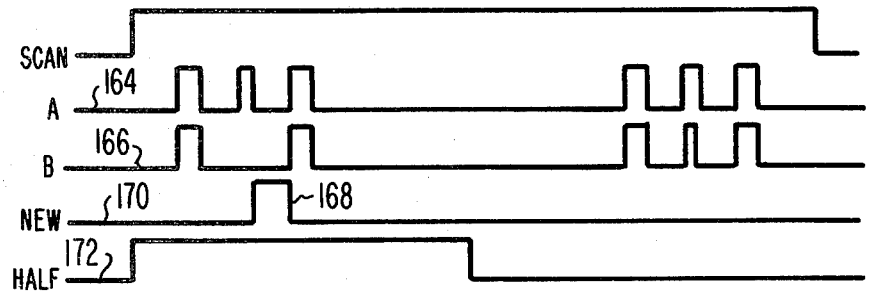
FIG. 13 is a schematic diagram showing a series of waveforms produced by the circuit of FIG. 11 during the scans shown in FIG. 12.

The functioning of the skew unit 158 is illustrated with respect to FIGS. 12 and 13. Two scans, A and B, that just touch or just miss the top of a slit 162 are shown. Signal 164 is the real time scan from Scan A emerging from the video processing circuits 152 and signal 166 is the delayed scan from Scan B emerging from the scan storage circuit 154. Presence of a pulse in Scan A and absence of a pulse in Scan B causes the skew unit 158 to generate a signal 170 labeled "New" which has a pulse 168 indicative of this difference. Analysis of the signal 170 with respect to a signal 172 related to half the scan time gives an indication whether the camera and pattern are aligned. If the camera is misaligned, either a CW or CCW light 174 and 176 respectively will flash continually, but when aligned, both indicators will sporadically flash.

The "New" signal 170 from the skew unit 158 is fed into a classification circuit 178. Two decisions must be made in the classification circuit 178. First, the type of pattern, whether dot or line, must be determined and next, if it is a line pattern, a rough estimate of element-to-element or "a" spacing must be established. To establish a type of pattern, blank scans are monitored. If blank scans occur within the pattern, then the plate is classified as a dot plate, since no blank scans will occur in a line pattern. By utilizing the "New" signal 170 and measuring distance to the next pattern element a number of times, a good indication of ½ of the "a" spacing is achieved. This value doubled is used in the comparative logic as a starting point, but is continually modified in a servo module 180, to follow "a" spacing variations. The classification 178 is primed by an outside signal 182 indicating when classification should occur. During classification, the "a" spacing is displayed for operator perusal.

Output from the "And" gate 160 is also fed into two variable length shift registers 184 and 186. These shift registers 184 and 186 are the center of the comparative logic. One register 184 has a maximum length of 32 stages and the other register 186 has a maximum length of 192 stages. In a standard shift register, all stages contain information, and when one bit is loaded at the serial input, all stages are triggered, and the last stage is dumped. In a FIFO type of register such as used in the present embodiment, the loading of the input is independent of the unloading of the output, so the amount of information contained within the register is variable. For example, data may be entered in bursts, and removed at uniform rates, the only requirement being that average rates over a period of time be identical. In the present embodiment, data corresponding to the first complete scan pattern is stored in the 192 stage register 186, (nominally 80 stages are used) and then when the second scan pattern data is received, the first and second scan patterns are shifted in parallel to the comparative logic. The register inputs are controlled by the input logic and the outputs are controlled by the servo module 180. Information when loaded will trickle into the registers as far as possible until it hits a stage that contains information. The first element loaded appears on the output in a manner of nanoseconds.

Outputs from each of the registers 184 and 186 are fed into two leading edge detector circuits 188 and 190. These circuits look for the loading edge of a scan pattern defined as a transition from a clear mask area, to an opaque area of a pattern element. Once this transition is detected, the signal is sent to the servo module 180 to determine if the transition is at the correct location to be the start of a scan pattern. Within each leading edge detector circuit there is filtering to compensate for the roughness of the edges of the pattern elements.

The servo module 180 is the control center for the system. Inputs to the servo module 180 come from the two leading edge detectors and information from the classification circuit 178 including type and initial "a" spacing. The servo module 180 then in turn controls the output of the two registers 184 and 186, updates the "a" spacing, and enables the comparative output logic. Initially, the first pattern is loaded into both registers 184 and 186 but is held only in the 192 stage register 186. The second pattern is loaded into both registers trickling to the end of the 32 stage register 184 but bumping up against the first pattern in the 192 stage register 186. When the leading edge of the second pattern is detected at the end of the 32 stage register 184, the outputs from both registers are stepped in unison, and the comparative logic is turned on. This process continues until end of scan. To allow for small variations of "a" spacing or for quantizing errors, the output of either shift register may be frozen, until the servo logic determines that both register outputs contain pattern leading edges. Within the servo logic, the "a" spacing is constantly updated to aid in the determination that an edge is a pattern leading edge, and not some defect.

Outputs from the two registers 184 and 186 and from the servo module 180 are fed into a correlation algorithm circuit 194. This circuit 194 consists of a full adder that may be wired to act as a majority gate. In this application, the adder looks at 5 pattern elements of both registers 184 and 186 in parallel, and if 3 or more pairs are identical, then a miscorrelation signal is not generated. A miscorrelation signal is only generated when less than 3 pairs match.

The sensitivity of the basic compare circuit in the correlation algorithm circuit 194 may be modified by manual activation at a mode switch 196. One of the 5 bits of pattern element information may be either forced true or false thereby changing the basic 3/5 to either 2/4 or ¾ weighting. Also, via the switch 196, the compare circuit may look at either 5 adjacent pattern elements or 5 alternately spaced pattern elements. Another option is to select one mode for the clear mask area and another mode for the opaque mask area. FIG. 14 is a table showing the various modes available. The first number in the top row and the left hand side column indicates whether each pattern element (1) or every other pattern element (½) is analyzed. The second number indicates the correlation level required to be acceptable. The numbers in the top row refer to the opaque pattern element, and the numbers down the left side refer to the clear areas of the pattern. For example, Mode 7 sets the following criteria.

Clear area of pattern all pattern elements are analyzed, and in any group of 4, three pairs must be identical.

Opaque area of pattern only every other pattern element is analyzed and in any group of 5 pattern elements, three pairs must be identical.

False miscorrelation at or near the ends of a pattern element may be caused by skew introduced by the mechanical motion of the camera, minute variations of element lengths, or by normal quantizing errors on the video signal.

To eliminate these false errors, it is required that for a miscorrelation to be identified as an error, it must occur in two consecutive scans at the same location. This is accomplished by first loading a miscorrelation signal into a scan storage shift register 198, and if on the following scan another miscorrelation occurs at some spot, an "And" gate 200 is satisfied and an error is indicated.

To aid an operator in monitoring the performance of the scanner, a two digit display 202 connected to a multiplexer 204 is provided. During initialization, the initial "a" spacing, fed from the classification circuit 178, is displayed, but once the unit starts scanning the full pattern, the updated "a" spacing from the servo module 180 is displayed. The multiplexor 204 is controlled by the prime signal 182 to gate the proper signals to the display.

I claim:

1. An inspection system for detecting defects in regular patterns wherein the elements of the patterns have variations in spatial period, said system comprising
   means for scanning and detecting the elements of a pattern to produce an original output signal indicative of the pattern,
   means for delaying the output signal from said scanning and detecting means to produce a delayed output signal,
   means for detecting deviation in period between the original output signal and the delayed output signal,
   means for matching the periods of said original and delayed output signals, and
   means for correlating the matched original and delayed output signals.

2. The inspection system as defined in claim 1 wherein said means for matching includes means for varying the scanning rate of the scanning and detecting means to maintain a constant period of the original output signal in response to a deviation in period from said means for detecting.

3. The inspection system as defined in claim 2 wherein said means for varying the scanning rate includes a clock frequency control.

4. An inspection system for detecting defects in regular patterns wherein the elements of the patterns have variations in spatial period, said system comprising
   means for scanning and detecting the elements of a pattern, to produce an output signal indicative of the pattern,
   means for detecting deviations from constancy in the period of the output signal and for generating an error signal related to the detected deviations, and
   means for varying the scanning rate of the scanning and detecting means to maintain a constant period at the output signal in response to the error signal.

5. The inspection system as defined in claim 4 including
   means for delaying the output signal, and
   means for correlating the delayed output signal with the original output signal.

6. The inspection system as defined in claim 5 wherein said means for correlating comprises means for subtracting the delayed output signal from the original output signal,
   whereby any remaining signal is an indication of a defect in the pattern.

7. The inspection system as defined in claim 6 including
   means for gating any remaining signal from said means for subtracting to obtain a dominant defect signal.

8. An inspection system for detecting defects in regular patterns wherein the elements of the patterns have variations in spatial period, said system comprising
   a video sensor,
   a platform movable in two directions upon which said video sensor is mounted,
   a first circuit for linearizing a scan rate of said video sensor over a regular pattern, said first circuit including a first portion and a second portion parallel with said first portion, said second portion including a delay line, said first circuit further including gate means and differential amplifier means for comparing the periods of the signals in said two portions and for producing a scan rate signal related to the difference in periods, and
   a second circuit for autocorrelating the output signal from said video sensor, said second circuit including two parallel portions one of which includes a delay line, said two parallel portions of said second circuit connected to the inputs of a differential amplifier.

* * * * *